United States Patent [19]

Wilk

[11] Patent Number: 5,312,417
[45] Date of Patent: May 17, 1994

[54] LAPAROSCOPIC CANNULA ASSEMBLY AND ASSOCIATED METHOD

[76] Inventor: Peter J. Wilk, 185 West End Ave., New York, N.Y. 10023

[21] Appl. No.: 921,511

[22] Filed: Jul. 29, 1992

[51] Int. Cl.⁵ .............................................. A61B 17/32
[52] U.S. Cl. ...................................... 606/114; 606/1; 606/127; 604/264
[58] Field of Search ................ 606/1, 108, 110, 113, 606/114, 119, 121, 122, 123, 127, 192, 198; 128/749; 604/90, 104–109, 264

[56] References Cited

U.S. PATENT DOCUMENTS

| | | | |
|---|---|---|---|
| 30,471 | 10/1960 | Dudley | 606/127 |
| 3,472,230 | 10/1969 | Fogarty | 606/127 |
| 3,794,044 | 2/1974 | Vennard et al. | 606/123 |
| 3,882,852 | 5/1975 | Sinnreich | 606/192 |
| 4,990,151 | 2/1991 | Wallsten | 606/108 |
| 5,011,488 | 4/1991 | Ginsburg | 604/104 |
| 5,176,687 | 1/1993 | Hasson et al. | 606/114 |
| 5,190,555 | 3/1993 | Wetter et al. | 606/127 |
| 5,190,561 | 3/1993 | Graber | 606/127 |

FOREIGN PATENT DOCUMENTS 2739589  3/1979  Fed. Rep. of Germany ...... 606/119

Primary Examiner—Stephen C. Pellegrino
Assistant Examiner—Glenn Dawson
Attorney, Agent, or Firm—R. Neil Sudol; Henry D. Coleman

[57] ABSTRACT

A cannula device for use in laparoscopic surgery includes a rigid tubular member and an expandable receiver connected to a distal end of the tubular member. The receiver portion of the cannula expands from a substantially cylindrical configuration to an expanded pocket for receiving a severed organ or organ part, thereby facilitating removal of the severed organ from a patient's abdomen during a laparoscopic surgical procedure.

17 Claims, 1 Drawing Sheet

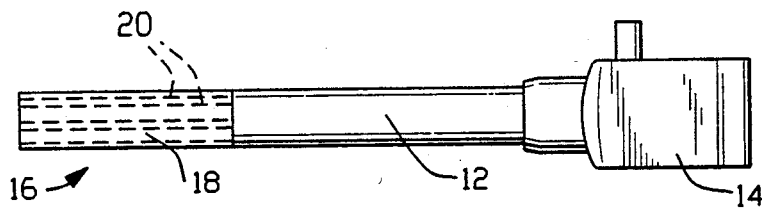
FIG. 1
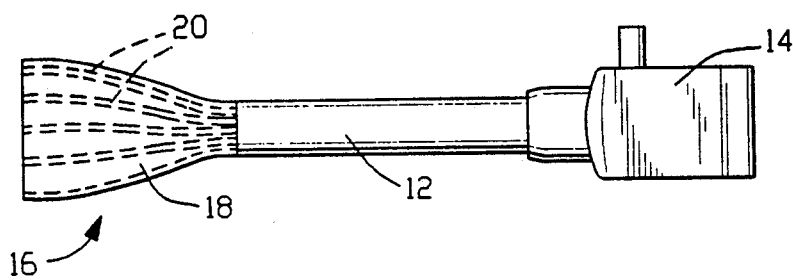
FIG. 2
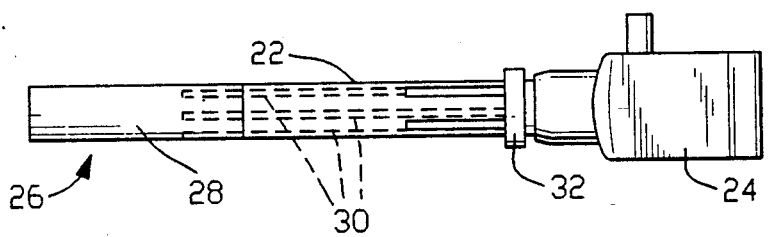
FIG. 3
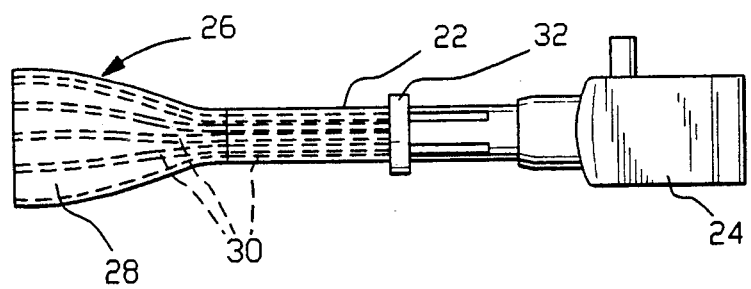
FIG. 4
FIG. 5
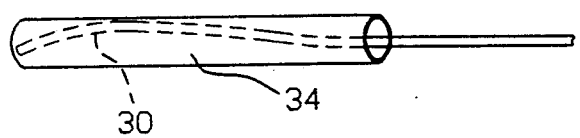
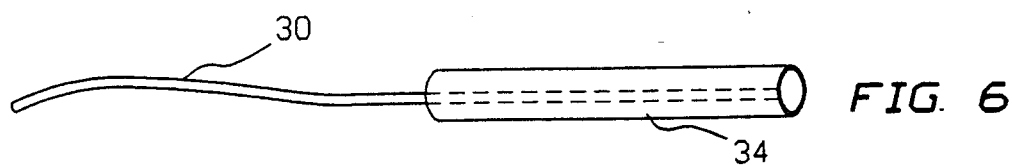
FIG. 6

LAPAROSCOPIC CANNULA ASSEMBLY AND ASSOCIATED METHOD

BACKGROUND OF THE INVENTION

This invention relates to a laparoscopic cannula assembly or a trocar sleeve assembly. This invention also relates to a laparoscopic surgical technique involving such a cannula assembly.

Laparoscopy involves the piercing of a patient's abdominal wall and the insertion of a cannula through the perforation. Generally, the cannula is a trocar sleeve which surrounds a trocar during an abdomen piercing operation. Upon the formation of the abdominal perforation, the trocar is withdrawn while the sleeve remains traversing the abdominal wall. A laparoscopic instrument, such as a laparoscope or a forceps, is inserted through the cannula so that a distal end of the instrument projects into the abdominal cavity.

Generally, in a laparoscopic surgical procedure, three or four perforations are formed in the abdomen to enable deployment of a sufficient number of laparoscopic instruments to perform the particular surgery being undertaken. Each perforation is formed by a trocar which is surrounded by a sleeve, the sleeves or cannulas all remaining in the abdominal wall during the surgical procedure.

Prior to insertion of the first trocar and its sleeve, a hollow needle is inserted through the abdominal wall to enable pressurization of the abdominal cavity with carbon dioxide. This insufflation procedure distends the abdominal wall, thereby producing a safety space above the patient's abdominal organs.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

Laparoscopic surgery is frequently performed to remove a malfunctioning organ such as a gall bladder filled with stones. Generally, a severed bladder is removed from the patient's abdomen by drawing the organ against the distal end of the trocar sleeve and then withdrawing the trocar sleeve with the bladder entrained thereto.

OBJECTS OF THE INVENTION

An object of the present invention is to provide a method for facilitating laparoscopic surgery, particularly surgery involving the removal of a severed organ or organ part.

An associated object of the present invention is to provide a trocar sleeve or laparoscopic cannula which facilitates the removal of a severed organ or organ part.

Another, more particular, object of the present invention is to provide such an instrument assembly which is simple to manufacture and therefore inexpensive.

A further particular object of the present invention is to provide such an instrument assembly which is easy to use.

These and other objects of the present invention will be apparent from the drawings and detailed descriptions herein.

SUMMARY OF THE INVENTION

A cannula device for use in laparoscopic surgery comprises, in accordance with the present invention, a rigid tubular member and an expandable receiver connected to the tubular member for expanding, from a substantially cylindrical configuration to an expanded pocket, a distal end of the tubular member to receive a severed organ or organ part, thereby facilitating removal of the severed organ from a patient's abdomen during a laparoscopic surgical procedure.

According to another feature of the present invention, an actuator mechanism is operatively connected to the tubular member and the receiver for expanding the receiver. In that connection, the actuator mechanism may be coupled to a plurality of at least partially arcuate ribs slidably mounted in a straightened configuration to the tubular member. The actuator mechanism slides the ribs in a distal direction relative to the tubular member. Alternatively, a tubular sheath may be provided over the distal end portion of the cannula device, the sheath being shiftable in the proximal direction for releasing for expansion a spring biased receiver at the distal end of the tubular member.

Pursuant to another feature of the present invention, the receiver includes a web and a plurality of ribs connected to the web. More particularly, the web may have a funnel shape with the ribs extending longitudinally along the web.

A method for use in laparoscopy comprises, in accordance with the present invention, the steps of (a) forming a perforation in a patient's abdominal wall, (b) disposing in the perforation a cannula assembly including at least one rigid tubular member, (c) severing an internal abdominal organ of the patient, (d) pulling the organ in a proximal direction towards the cannula assembly, (e) expanding a distal end portion of the cannula assembly, (f) drawing the organ into the expanded distal end portion of the cannula assembly, and (g) removing the cannula assembly, together with the severed organ, from the patient.

According to specific embodiment of the present invention, the expansion of the distal end portion of the cannula assembly is coincidental with the drawing of the severed organ into the distal end portion of the cannula. In that event, the step of drawing causes the expansion of the distal end portion of the cannula assembly. According to another, alternative, embodiment of the present invention, the expansion of the distal end portion of the cannula assembly is executed prior to the step of drawing. In that event, an actuator mechanism is advantageously provided for effectuating the expansion of the receiver portion of the cannula. More particularly, expanding the distal end portion of the cannula may include the steps of shifting a plurality of ribs in a distal direction along the cannula and bending the ribs in a radial direction.

A surgical technique and associated device in accordance with the present invention will facilitate the removal of organs and organ parts via laparoscopic procedures. The possibility that the severed organ will tear away or become dislodged while being pulled through the abdominal wall is practically eliminated. In addition, the technique is simpler than recently developed procedures wherein the severed organ is placed into a plastic pouch or bag inside the abdomen.

A surgical technique in accordance with the present invention is easy to implement and will not require inordinately extensive instruction or experience to master.

A surgical instrument assembly utilizable in performing a method in accordance with the present invention is simple to manufacture and therefore inexpensive.

BRIEF DESCRIPTION OF THE DRAWING

FIG. 1 is a side elevational view of a laparoscopic cannula in accordance with the present invention, showing an expandable distal end portion in a collapsed configuration.

FIG. 2 is a view similar to FIG. 1, showing the distal end portion of the cannula of FIG. 1 in an expanded configuration for receiving a severed internal organ of a patient.

FIG. 3 is a side elevational view of another laparoscopic cannula in accordance with the present invention, showing an expandable distal end portion in a collapsed configuration.

FIG. 4 is a view similar to FIG. 3, showing the distal end portion of the cannula of FIG. 3 in an expanded configuration for receiving a severed internal organ of a patient.

FIG. 5 is a schematic perspective view of a spring biased expander rib shown in FIGS. 3 and 4, illustrating the rib in a straightened configuration inside a holding channel.

FIG. 6 is a view similar to FIG. 5, showing the rib of FIG. 5 in an extended and expanded configuration.

DETAILED DESCRIPTION

As illustrated in FIG. 1, a laparoscopic cannula or trocar sleeve for use in laparoscopic surgery comprises a rigid tubular member 12 with an insufflation port component 14 at a proximal end and an expandable receiver portion 16 at a distal end. Receiver portion 16 expands from a substantially cylindrical insertion configuration shown in FIG. 1 to an expanded cupshaped pocket shown in FIG. 2. Receiver portion 16 includes an elastic or pleated web 18 provided along an inner surface with a plurality of longitudinally extending resilient ribs 20. Ribs 20 have an internal spring bias tending to maintain the ribs in a straightened configuration (FIG. 1). However, upon a pulling of a severed organ or organ part into the distal end of receiver portion 16, ribs 20 expand outwardly, thereby permitting a surgeon to pull the severed organ into web 18. The severed organ or organ part is drawn into the distal end of receiver portion 16 by a conventional laparoscopic instrument such as a grasping forceps of laparoscopic clamp. Upon a drawing of the severed organ into receiver portion 16, the entire cannula is withdrawn from the abdominal wall of the patient.

FIGS. 1 and 2 show ribs 20 disposed along an inner side of web 18. However, ribs 20 may alternatively be attached to the outer surface of web 18.

As illustrated in FIGS. 3 and 4, another laparoscopic cannula or trocar sleeve for use in laparoscopic surgery comprises a rigid tubular member 22 with an insufflation port component 24 at a proximal end and an expandable receiver portion 26 at a distal end. Receiver portion 26 expands from a substantially cylindrical insertion configuration depicted in FIG. 3 to an expanded pocket or pouch shown in FIG. 4. Receiver portion 26 includes an elastic or pleated web 28 provided along an inner surface with a plurality of longitudinally extending resilient ribs (not illustrated) which have an internal spring bias tending to maintain the ribs in a straightened configuration (FIG. 3).

The cannula of FIGS. 3 and 4 is additionally provided with a plurality of longitudinally extending ribs 30 which are slidably mounted to tubular member 22. Ribs 30 are connected to an annular actuator 32 which surrounds tubular member 22. Ribs 30 have an internal spring bias which tends to form the ribs into an arcuate configuration. While inside tubular member 22, ribs 30 are constrained to retain a substantially straightened configuration. To that end, ribs 30 may be disposed inside channels or conduits 34 (FIGS. 5 and 6) provided on tubular member 22.

Prior to and during a disposing of the cannula of FIG. 3 in a patient's abdominal wall, ribs 30 are retracted into tubular member 22 and particularly into respective channels 34 provided along an inner side of tubular member 22, as illustrated in FIG. 5. Receiver portion 26 is maintained substantially in a tubular configuration by ribs (not shown) attached to web 28, as shown in FIG. 3.

Prior to a drawing of a severed organ or organ part towards receiver portion 26 of tubular member 22, actuator ring 32 is pushed in a distal direction to eject ribs 30 from tubular member 22. During ejection from tubular member 22, ribs 30 each assume an arcuate configuration (see FIG. 6) under the action of their internal spring bias and press web 28 outwardly so that the web assumes an expanded cup-shaped configuration (FIG. 4) permitting a surgeon to pull the severed organ into web 28. Upon a drawing of the severed organ into receiver portion 26, the entire cannula is withdrawn from the abdominal wall of the patient.

It is to be noted that ribs 20 (FIGS. 1 and 2), as well as the corresponding ribs in the embodiment of FIGS. 3 and 4, maintained webs 18 and 28 in substantially cylindrical configurations aligned with and extending distally from the respective tubular members 12 and 22. Accordingly, the webs are relaxed or unstressed in the cylindrical configurations and expand outwardly only upon an application of external forces, e.g., through slidable ribs 30 (FIG. 4) or through the pulling of an organ part into the web (FIG. 2).

Although the invention has been described in terms of particular embodiments and applications, one of ordinary skill in the art, in light of this teaching, can generate additional embodiments and modifications without departing from the spirit of or exceeding the scope of the claimed invention. For example, the distal end portion of a cannula assembly in accordance with the present invention may be provided with ribs which have an inherent spring bias tending to force the distal end portion of the cannula assembly into an expanded configuration. During insertion of the cannula assembly, the ribs may be held in a straightened configuration by an auxiliary tube slidably disposed outside of the cannula. Upon disposition of the cannula assembly in the patient's abdominal wall and prior to the drawing of a severed organ into the cannula assembly, the tubular member is shifted in a proximal direction to enable expansion of the ribs under the action of their own internal forces. The ribs may be attached to a pleated or elastic web. However, a web is not necessary.

Expansion of the distal end portion of the distal end portion of the cannula assembly may be accomplished by techniques which are more complicated than those described hereinabove with reference to the drawings. For example, a hydraulic or pneumatic circuit may be connected to expanded balloon components at the distal end of the cannula assembly. The balloon components may be transversely oriented rings or longitudinally oriented ribs.

In another embodiment in accordance with the present invention, the entire distal end portion of the cannula assembly constitutes an expandable skirt which is slidably connected to the rigid distal end portion of the cannula. In a retracted configuration, the skirt is collapsed, in an essentially cylindrical shape. Upon extension of the skirt in the distal direction, the skirt expands under the action of its internal spring biasing to an opened configuration for received a severed organ.

Accordingly, it is to be understood that the drawings and descriptions herein are proferred by way of example to facilitate comprehension of the invention and should not be construed to limit the scope thereof.

What is claimed is:

1. A trocar sleeve device for use in laparoscopic surgery, comprising:
    a rigid tubular member provided at a proximal end with a permanently attached insufflation port component;
    expandable resilient receiver means, connected to said tubular member at a distal end thereof opposite said proximal end and having when relaxed a substantially oylindrical configuration aligned with and extending distally from said tubular member, for expanding from said cylindrical configuration to an expanded pocket to receive a severed organ or organ part, thereby facilitating removal of the severed organ from a patient's abdomen during a laparoscopic surgical procedure; and
    means attached to said receiver means for maintaining said receiver means in said cylindrical configuration in the absence of external forces on said receiver means.

2. The device defined in claim 1, further comprising expansion means operatively connected to said tubular member and said receiver means for expanding said receiver means.

3. The device defined in claim 2 wherein said expansion means includes a plurality of at least partially arcuate ribs slidably mounted in a straightened configuration to said tubular member.

4. The device defined in claim 3 wherein said expansion means further includes actuator means operatively connected to said ribs for sliding said ribs in a distal direction relative to said tubular member.

5. The device defined in claim 1 wherein said receiver means includes a web and wherein said means for maintaining includes a plurality of ribs connected to said web.

6. The device defined in claim 5 wherein said web has a funnel shape in an expanded, stressed configuration of said receiver means and wherein said ribs extend longitudinally along said web.

7. A method for use in laparoscopy, comprising the steps of:
    forming a perforation in a patient's abdominal wall;
    providing a cannula assembly including at least one rigid tubular member with a resiliently expandable distal end portion having a substantially cylindrical configuration when relaxed;
    disposing said cannula assembly in said perforation so that said tubular member is in direct contact with the patient's abdominal wall tissues at said perforation;
    severing an internal abdominal organ of the patient;
    pulling said organ in a proximal direction into said cannula assembly to thereby expand said distal end portion of said cannula assembly from said cylindrical configuration; and
    removing said cannula assembly, together with the severed organ, from the patient.

8. The method defined in claim 7, further comprising the step of partially contracting said distal end portion prior to completion of said step of removing.

9. A method for use in laparoscopy, comprising the steps of:
    forming a perforation in a patient's abdominal wall;
    providing a cannula assembly including at least one rigid tubular member with a resiliently expandable distal end portion having a substantially cylindrical configuration extending distally from said tubular member when relaxed, said cannula assembly further having an actuator slidably attached to said tubular member;
    disposing said cannula assembly in said perforation so that said tubular member is in direct contact with the patient's abdominal wall tissues at said perforation;
    severing an internal abdominal organ of the patient;
    shifting said actuator in a distal direction along said tubular member to expand said distal end portion from said cylindrical configuration;
    pulling said organ in a proximal direction into the expanded distal end portion of said cannula assembly; and
    removing said cannula assembly, together with the severed organ, from the patient.

10. The method defined in claim 9 wherein said step of shifting includes the steps of shifting a plurality of ribs in a distal direction along said cannula assembly and bending said ribs in a radial direction.

11. The method defined in claim 9, further comprising the step of partially contracting said distal end portion prior to completion of said step of removing.

12. A trocar sleeve device for use in laparoscopic surgery, comprising:
    a rigid tubular member provided at a proximal end with a permanently attached insufflation port component; and
    expandable receiver means connected to said tubular member at a distal end thereof, opposite said insufflation port component, for expanding from a substantially cylindrical configuration to an expanded pocket to receive a severed organ or organ part, thereby facilitating removal of the severed organ from a patient's abdomen during a laparoscopic surgical procedure, said receiver means having a spring bias tending to maintain said receiver means in said cylindrical configuration aligned with said tubular member and extending in a distal direction therefrom.

13. The device defined in claim 12, further comprising expansion means operatively connected to said tubular member and said receiver means for expanding said receiver means.

14. The device defined in claim 13 wherein said expansion means includes a plurality of at least partially arcuate ribs slidably mounted in a straightened configuration to said tubular member.

15. The device defined in claim 14 wherein said expansion means further includes actuator means operatively connected to said ribs for sliding said ribs in a distal direction relative to said tubular member.

16. The device defined in claim 12 wherein said receiver means includes a web and a plurality of ribs connected to said web, said ribs providing said spring bias.

17. The device defined in claim 16 wherein said web has a funnel shape in an expanded configuration and wherein said ribs extend longitudinally along said web.

* * * * *